US011219429B2

(12) United States Patent
Shin et al.

(10) Patent No.: US 11,219,429 B2
(45) Date of Patent: Jan. 11, 2022

(54) ULTRASOUND IMAGING APPARATUS AND CONTROLLING METHOD FOR THE SAME (71) Applicant: SAMSUNG MEDISON CO., LTD., Gangwon-do (KR)

(72) Inventors: Dong Kuk Shin, Guri-si (KR); Dal Kwon Ko, Seoul (KR); Jong-Sik Kim, Seoul (KR); Soo-young Oh, Seoul (KR); Dong-Wook Kwak, Seoul (KR); Kunwoo Kim, Seoul (KR); Moon Young Kim, Seoul (KR); Hyun Soo Park, Goyang-si (KR); Hyun-Joo Seol, Seoul (KR); Sae Kyung Choi, Seoul (KR); Joon Seok Hong, Seoul (KR); Han Sung Hwang, Goyang-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 593 days.

(21) Appl. No.: 15/770,094

(22) PCT Filed: Oct. 12, 2016

(86) PCT No.: PCT/KR2016/011412
§ 371 (c)(1),
(2) Date: Apr. 20, 2018

(87) PCT Pub. No.: WO2017/069451
PCT Pub. Date: Apr. 27, 2017

(65) Prior Publication Data
US 2018/0303460 A1 Oct. 25, 2018

(30) Foreign Application Priority Data
Oct. 20, 2015 (KR) .................. 10-2015-0146212

(51) Int. Cl.
A61B 8/08 (2006.01)
A61B 8/00 (2006.01)
G06T 7/00 (2017.01)

(52) U.S. Cl.
CPC .............. *A61B 8/485* (2013.01); *A61B 8/463* (2013.01); *A61B 8/469* (2013.01); *A61B 8/5207* (2013.01);
(Continued)

(58) Field of Classification Search
CPC ....... A61B 8/485; A61B 8/5207; A61B 8/463; A61B 8/467; A61B 8/469; A61B 8/5215;
(Continued)

(56) References Cited

U.S. PATENT DOCUMENTS

2009/0030314 A1* 1/2009 Kawae ................. A61B 8/0866
600/443
2015/0005630 A1 1/2015 Jung et al.
(Continued)

FOREIGN PATENT DOCUMENTS

CN 101061511 A 10/2007
KR 10-2007-0021420 A 2/2007
(Continued)

OTHER PUBLICATIONS

Molina, F. S., L. F. Gomez, J. Florido, M. C. Padilla, and K. H. Nicolaides. "Quantification of cervical elastography: a reproducibility study." Ultrasound in Obstetrics & Gynecology 39, No. 6 (2012): 685-689.*
(Continued)

*Primary Examiner* — Carolyn A Pehlke
(74) *Attorney, Agent, or Firm* — Morgan, Lewis & Bockius LLP (57) ABSTRACT Disclosed herein is an ultrasound imaging apparatus capable of setting a region of interest having a shape corresponding
(Continued)

to a shape of the cervix canal in an elasticity image of the cervix and displaying the region of interest, and a control method thereof. The ultrasound imaging apparatus includes a display unit configured to display an ultrasound elasticity image and a controller configured to select a point included in a path corresponding to the cervix canal in the elasticity image of the cervix displayed on the display unit, configured to set a region of interest having a shape corresponding to a shape of at least one portion of the cervix canal based on the selected point, and configured to display the region of interest on the display unit.

8 Claims, 7 Drawing Sheets

(52) U.S. Cl.
CPC .......... *A61B 8/5215* (2013.01); *G06T 7/0012* (2013.01); *A61B 8/085* (2013.01); *A61B 8/0866* (2013.01)

(58) Field of Classification Search
CPC ....... A61B 8/0866; A61B 8/08; A61B 8/0858; G06T 7/0012
See application file for complete search history.

(56) References Cited

U.S. PATENT DOCUMENTS

| | | |
|---|---|---|
| 2015/0148674 A1 | 5/2015 | Park et al. |
| 2015/0148676 A1 | 5/2015 | Choi et al. |
| 2015/0209011 A1 | 7/2015 | Lee |
| 2017/0251999 A1* | 9/2017 | Noguchi ................ A61B 8/463 |

FOREIGN PATENT DOCUMENTS

| | | |
|---|---|---|
| KR | 10-2012-0122455 A | 11/2012 |
| KR | 10-2015-0089837 A | 8/2015 |
| WO | 2012/148188 A2 | 11/2012 |

OTHER PUBLICATIONS

To, M. S., C. Skentou, C. Chan, A. Zagaliki, and K. H. Nicolaides. "Cervical assessment at the routine 23-weekscan: standardizing techniques." Ultrasound in Obstetrics and Gynecology: The Official Journal of the International Society of Ultrasound in Obstetrics and Gynecology 17, No. 3 (2001): 217-219.*

Written Opinion and International Search Report dated Jan. 25, 2017 issued in International Patent Application No. PCT/KR2016/011412.

Extended Search Report issued in corresponding European Application No. 16857709.6, dated Jun. 12, 2019.

E. Hernandez-Andrade, et al. "Evaluation of cervical stiffness during pregnancy using semiquantitative ultrasound elastography," Ultrasound Obstet Gynecol, 2013, vol. 41, pp. 152-161.

Chinese Office Action dated Jun. 2, 2020 issued in Chinese Patent Application No. 201680061709.X.

Chinese Office Action dated Jan. 28, 2021 issued in Chinese Patent Application No. 201680061709.X (with English translation).

* cited by examiner

ULTRASOUND IMAGING APPARATUS AND CONTROLLING METHOD FOR THE SAME

CROSS REFERENCE

This patent application is the U.S. National Phase under 35 U.S.C. § 371 of International Application No. PCT/KR2016/011412, filed on Oct. 12, 2016, which claims the benefit of Korean Patent Application No. 10-2015-0146212, filed on Oct. 20, 2015, the entire contents of each are hereby incorporated by reference.

TECHNICAL FIELD

Embodiments of the present disclosure relate to an ultrasound imaging apparatus configured to generate an image of the inside of an object by using ultrasonic waves.

BACKGROUND ART

An ultrasound imaging apparatus irradiates ultrasound signals to a target part inside an object from the surface of an object, and noninvasively acquires section images about soft tissue of the object or images about blood vessels of the object by using echo ultrasound signals reflected from the object.

An ultrasound imaging apparatus is compact, inexpensive, and displaying a diagnostic imaging immediately as compared with another type of diagnostic imaging apparatus, e.g., X-ray device, Computerized Tomography Scanner (CT), Magnetic Resonance Image (MRI), diagnostic nuclear medical apparatus. In addition, the ultrasound imaging apparatus is safe because there is no risk of radiation exposure. Therefore, the ultrasound imaging apparatus is widely used in medical examination at cardiology, abdomen, urology, and maternity clinics.

The ultrasound imaging apparatus may include an ultrasound probe configured to send ultrasound signals to an object and receive ultrasound echo signal reflected from the object so as to acquire an ultrasound image of the object, and a body configured to generate an internal image of the object by using the ultrasound echo signal received from the ultrasound probe.

DISCLOSURE

Technical Problem

Therefore, it is an aspect of the present disclosure to provide an ultrasound image apparatus capable of setting a Region of Interest (ROI) having a shape corresponding to a shape of the cervix canal and displaying the ROI in an ultrasound elasticity image of the cervix.

Technical Solution

In accordance with one aspect of the present disclosure, an ultrasound imaging apparatus includes a display unit configured to display an ultrasound elasticity image; an input unit configured to receive an input of a command to select a point included in a path corresponding to the cervix canal in the ultrasound elasticity image of the cervix displayed on the display unit; and a controller configured to set a region of interest having a shape corresponding to a shape of at least one portion of the cervix canal and configured to display the region of interest on the display unit when the point included in a path corresponding to the cervix canal is selected via the input unit.

The point included in the path may include at least one of an external orifice of the uterus, an internal orifice of the uterus, and a feature point in the cervix canal.

The feature point may include a point corresponding to a curved portion of the cervix.

The controller may set a region of interest including a boundary having a shape corresponding to the path and being spaced apart with respect to the path corresponding to the cervix canal with a predetermined distance in directions that are opposite to each other.

The display unit may display a region of interest including a boundary having a shape corresponding to the path and being spaced apart with respect to the path corresponding to the cervix canal with a predetermined distance in directions that are opposite to each other.

The controller may calculate a ratio of an elasticity value of a first region including the cervix canal in the region of interest and an elasticity value of a second region that is outside of the first region.

The controller may calculate an elasticity value of the external orifice of the uterus, an elasticity value of the internal orifice of the uterus, and a ratio of the elasticity value of the external orifice of the uterus and the elasticity value of the internal orifice of the uterus.

In accordance with another aspect of the present disclosure, an ultrasound imaging apparatus includes a display unit configured to display an elasticity image of the cervix, and a region of interest having a shape corresponding to a shape of the cervix canal in the elasticity image; and a controller configured to calculate a ratio of an elasticity value of a first region including the cervix canal in the region of interest and an elasticity value of a second region that is outside of the first region.

The controller may calculate an elasticity value of an external orifice of the uterus, an elasticity value of an internal orifice of the uterus, and a ratio of the elasticity value of the external orifice of the uterus and the elasticity value of the internal orifice of the uterus.

The ultrasound imaging apparatus may further include an input unit configured to receive an input of a command to select a point included in a path corresponding to the cervix canal in the elasticity image of the cervix displayed on the display unit.

The controller may set a region of interest having a shape corresponding to a shape of the cervix canal, and display the region of interest on the display unit when the point included in a path corresponding to the cervix canal is selected via the input unit.

The point included in the path may include at least one of the external orifice of the uterus, the internal orifice of the uterus, and a feature point in the cervix canal.

The feature point may include a point corresponding to a curved portion of the cervix.

The controller may set a region of interest including a boundary having a shape corresponding to the path and being spaced apart with respect to the path corresponding to the cervix canal with a predetermined distance in directions that are opposite to each other.

The display unit may display a region of interest including a boundary having a shape corresponding to the path and being spaced apart with respect to the path corresponding to the cervix canal with a predetermined distance in directions that are opposite to each other.

In accordance with another aspect of the present disclosure, a control method of an ultrasound imaging apparatus includes receiving an input of a command to select a point included in a path corresponding to the cervix canal in an elasticity image of the cervix displayed on a display unit; setting a region of interest having a shape corresponding to a shape of the cervix canal when a point included in a path corresponding to the cervix canal is selected; and displaying the set region of interest on the display unit.

The set of the region of interest may include setting a region of interest including a boundary having a shape corresponding to the path and being spaced apart with respect to the path corresponding to the cervix canal with a predetermined distance in directions that are opposite to each other.

The display of the region of interest on the display unit may include displaying a region of interest including a boundary having a shape corresponding to the path and being spaced apart with respect to the path corresponding to the cervix canal with a predetermined distance in directions that are opposite to each other.

The control method may further include calculating a ratio of an elasticity value of a first region including the cervix canal in the region of interest and an elasticity value of a second region that is outside of the first region.

The control method may further include calculating an elasticity value of an external orifice of the uterus, an elasticity value of an internal orifice of the uterus, and a ratio of the elasticity value of the external orifice of the uterus and the elasticity value of the internal orifice of the uterus.

Advantageous Effects

In accordance with one aspect of the present disclosure, an ultrasound imaging apparatus may effectively acquire elasticity information of the cervix by setting a Region of Interest (ROI) having a shape corresponding to a shape of the cervix canal.

In accordance with another aspect of the present disclosure, an ultrasound imaging apparatus may provide effective information to determine an elasticity of the cervix by providing a ratio of an elasticity value of a first region that is around the cervix, and a second region that is outside of the first region with respect to the cervix canal.

DESCRIPTION OF DRAWINGS

These and/or other aspects of the present disclosure will become apparent and more readily appreciated from the following description of the embodiments, taken in conjunction with the accompanying drawings of which.

BEST MODE

Reference will now be made in detail to embodiments of the present disclosure, examples of which are illustrated in the accompanying drawings, wherein like reference numerals refer to like elements throughout.

Figure 1:
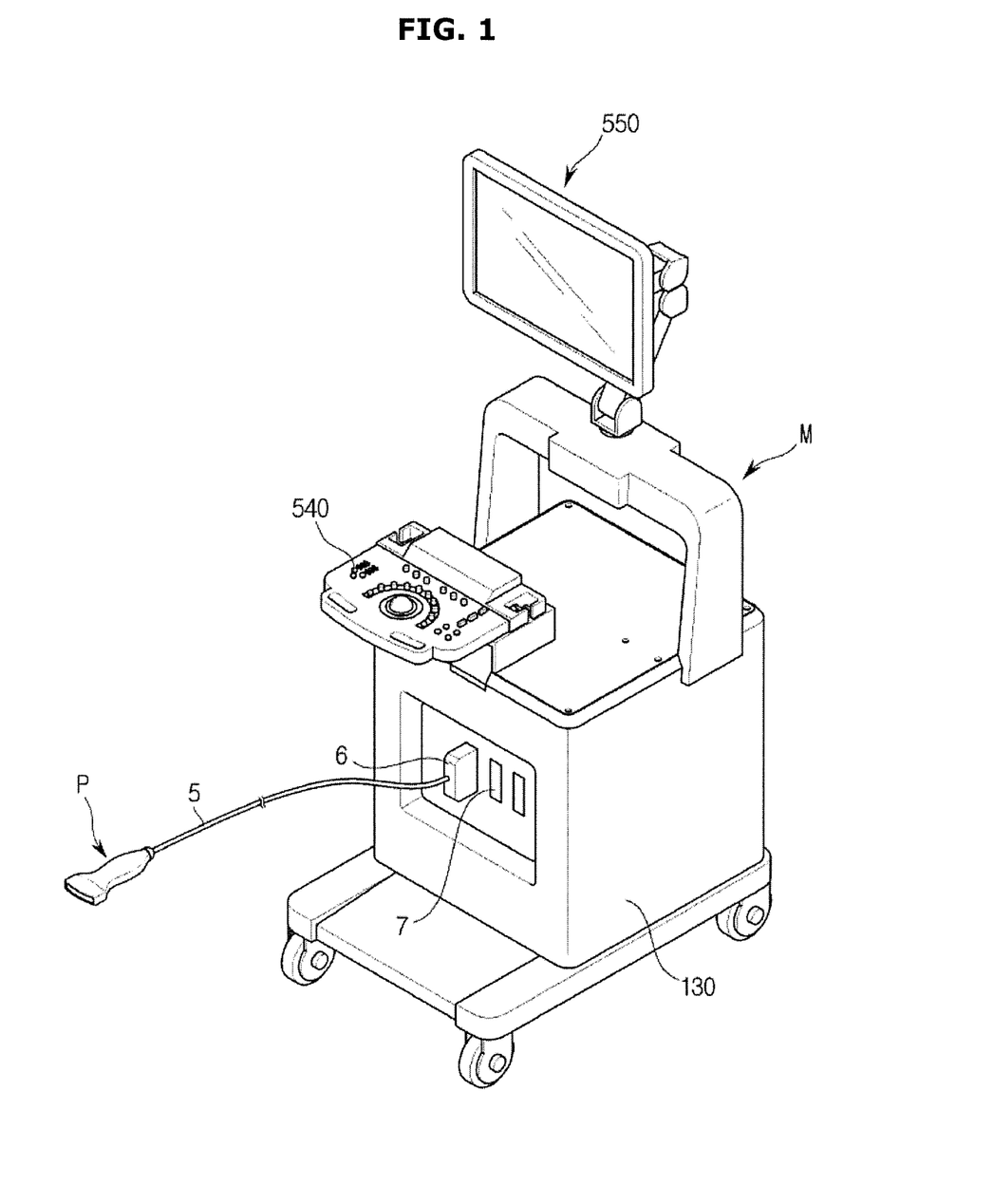
FIG. 1 is a view illustrating an exterior of an ultrasound imaging apparatus in accordance with an embodiment of the present disclosure.
Figure 2:
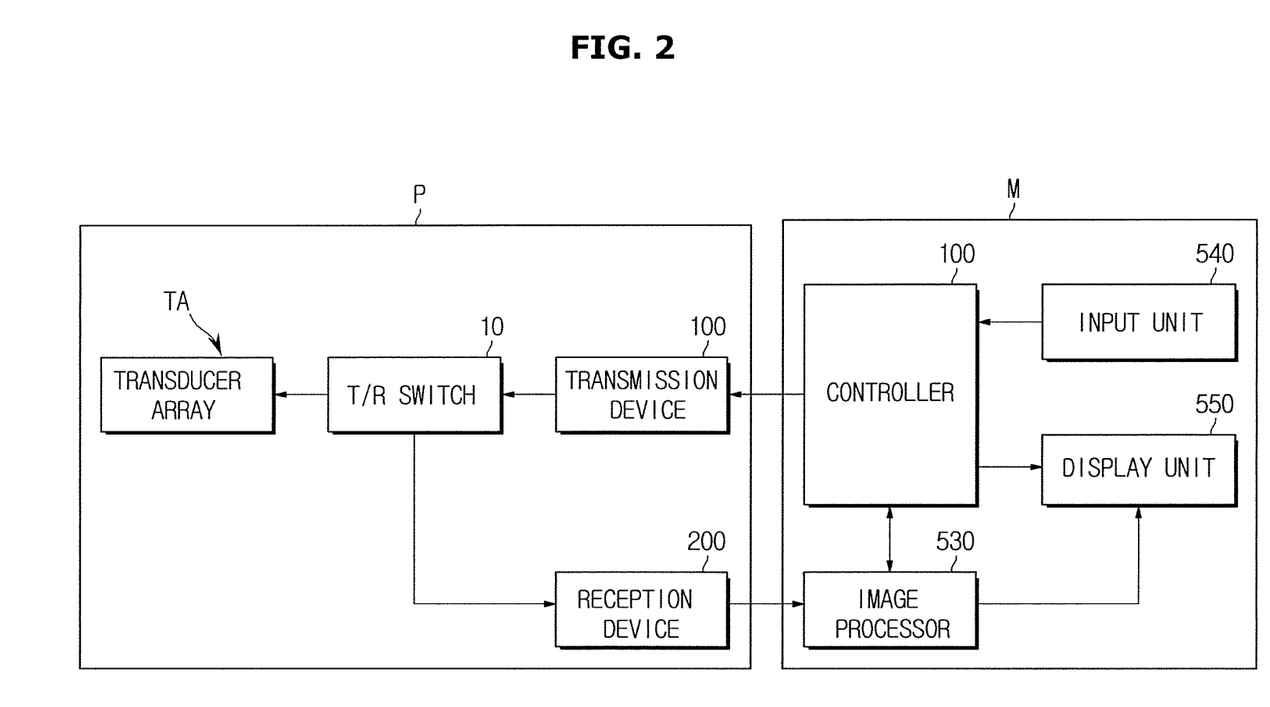
FIG. 2 is a control block diagram illustrating an ultrasound imaging apparatus in accordance with an embodiment of the present disclosure.
Figure 3:
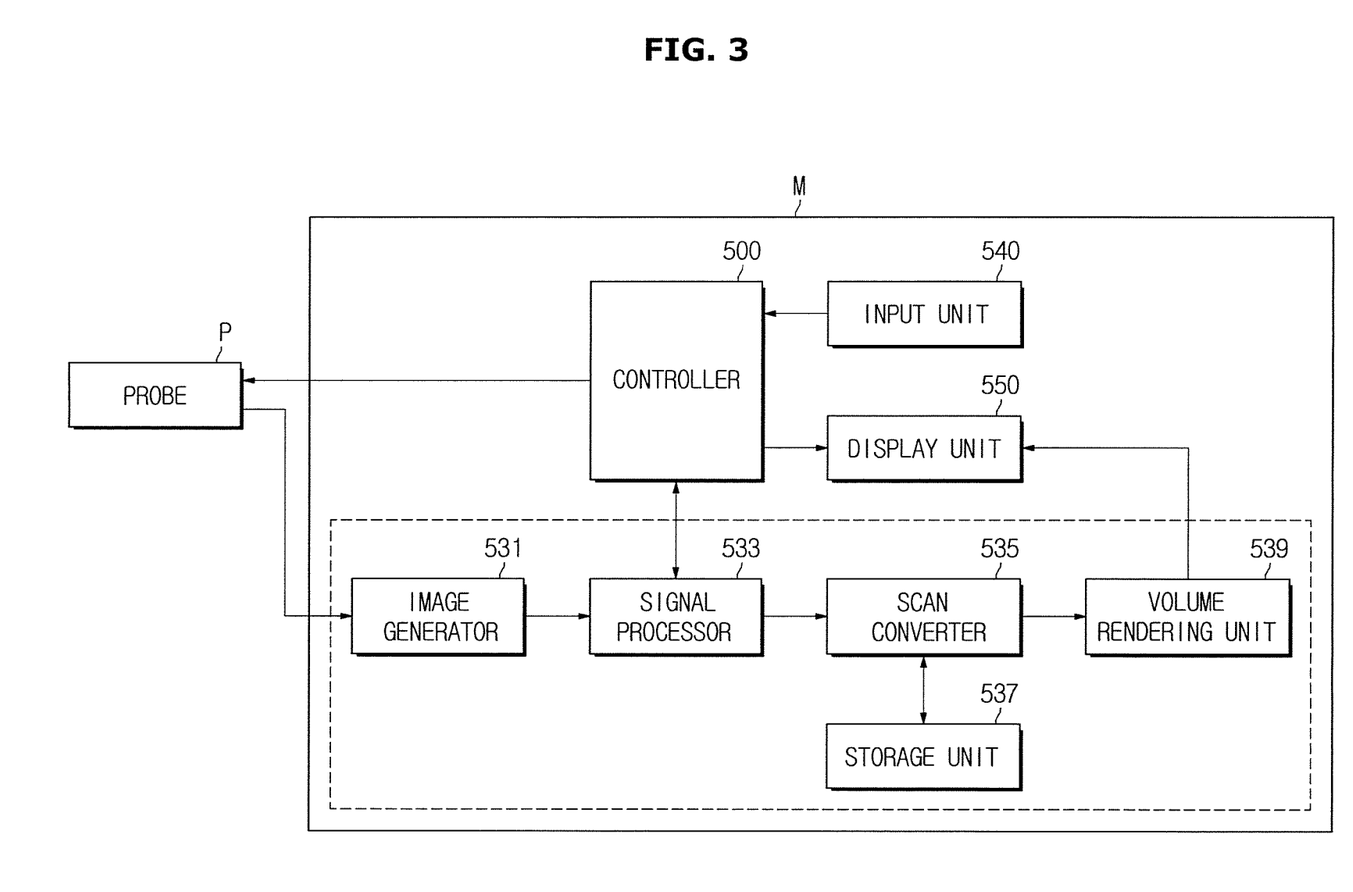
FIG. 3 is a control block diagram detailedly illustrating a configuration of a body of an ultrasound imaging apparatus in accordance with an embodiment of the present disclosure.

FIG. 1 is a view illustrating an exterior of an ultrasound imaging apparatus in accordance with an embodiment of the present disclosure, FIG. 2 is a control block diagram illustrating an ultrasound imaging apparatus in accordance with an embodiment of the present disclosure, and FIG. 3 is a control block diagram detailedly illustrating a configuration of a body of an ultrasound imaging apparatus in accordance with an embodiment of the present disclosure.

Referring to FIG. 1, an ultrasound imaging apparatus 1 may include an ultrasound probe (P) that sends ultrasonic waves to an object, receives ultrasound echo signal and convert the ultrasound echo signal into an electrical signal, and a body (M) that is connected to the probe (P) and displays an ultrasound image by including an input unit 540 and a display unit 550. The probe (P) may receive an input of a variety of signals that are needed for the control of the probe (P) by being connected to the body (M) of the ultrasound imaging apparatus via a cable 5, or may transmit an analog signal or a digital signal corresponding to an ultrasound echo signal received via the probe (P) to the body (M). However, an embodiment of the probe (P) is not limited thereto, and thus when the probe (P) is implemented by a wireless probe the probe (P) may send/receive a signal to/from the body (M) via a network formed therebetween.

One end of the cable 5 may be connected to the probe (P) and the other end of the 5 may be connected to a connector 6 that is coupled to or detached from a slot 7 of the body (M). The body (M) and the probe (P) may send/receive a control command or data with each other via the cable 5. For example, when a user inputs information related to a focal point depth, the size and the shape of aperture or a steering angle, the information may be transmitted to the probe (P) via the cable 5 and used for a transmission and reception beamforming of a transmission device 100 and a reception device 200. In addition, as mentioned above, when the probe (P) is implemented by a wireless probe, the probe (P) may be connected to the body (M) via the wireless network other than the cable 5. When the probe (P) is connected to the body (M) via the wireless network, the body (M) may send/receive the above mentioned control command or data to/from the probe (P). As illustrated in FIG. 2, the body (M) may include a controller 500, an image processor 530, an input unit 540, and a display unit 550.

The controller 500 may control an overall operation of the ultrasound imaging apparatus 1. Particularly, the controller 500 may generate a control signal to control each component of the ultrasound imaging apparatus 1, e.g. the transmission device 100, a T/R switch 10, the reception device 200, the image processor 530 and the display unit 550 as illustrated in FIG. 2, and control an operation of each of the above-mentioned component. According to an embodiment illustrated in FIGS. 2 and 3, in the ultrasound imaging apparatus, a transmission and reception beamformer may be included in the probe (P) other than the body, but the transmission and reception beamformer may be included in the body other than the probe (P).

The controller 500 may calculate a delay profile about a plurality of ultrasound transducer elements 60 forming an ultrasound transducer array (TA), and may calculate a time delay value according to a distance difference in a focal point of an object and the plurality of ultrasound transducer elements 60 included in the ultrasound transducer array (TA) based on the calculated delay profile. The controller 500 may allow a transmission and reception signal to be generated by controlling the transmission and reception beamformer.

The controller 500 may control the ultrasound imaging apparatus 1 by generating a control command to control each component of the ultrasound imaging apparatus 1 according to user' instruction or command, which is input via the input unit 540. According to an embodiment, the controller 500 may set a region of interest (ROI) to a shape corresponding to the ROI in an ultrasound elasticity image without setting the ROI to a circle or a square shape including the ROI in an ultrasound elasticity image. For example, the controller may set a ROI having a shape corresponding to a shape of the cervix that is an object to interest in an ultrasound elasticity image of the cervix and may display the ROI in the ultrasound elasticity image displayed on the display unit. A description thereof will be described.

The image processor 530 may generate an ultrasound image of a target part inside of an object based on an ultrasound signal focused through the reception device 200.

Referring to FIG. 3, the image processor 530 may include an image generator 531, a signal processor 533, a scan converter 535, a storage unit 537, and a volume rendering unit 539.

The image generator 531 may generate a coherent two dimensional image or a coherent three dimensional image of a target part inside of an object based on an ultrasound signal focused through the reception device 200.

The signal processor 533 may convert coherent image information generated by the image generator 531 into ultrasound image information according to a diagnosis mode, e.g. B-mode or Doppler mode. For example, when the diagnosis mode is set to B-mode, the signal processor 533 may perform a process, e.g. A/C conversion, and may generate ultrasound image information for B-mode image in real time. In addition, when the diagnosis mode is set to D-mode, the signal processor 533 may extract phase variation information from an ultrasound signal, calculate information, e.g. speed, power and distribution of blood flow corresponding to each point of a cross-sectional image, and generate ultrasound image information for D-mode image in real time.

When the diagnosis mode is set to elasticity mode, the signal processor 533 may estimate variation images from consecutive ultrasound images, extract a point in which a variation of the tissue occurs, and calculate a movement speed of the variation. In this case, the variation of the tissue may be detected by comparing consecutive ultrasound images by calculating a degree of variation of scatter. The signal processor 533 may identify a position of transverse waves in the image from the each variation image, estimate a propagation speed of the transverse waves, and calculate a shear modulus based on the propagation speed of transverse waves. The shear modulus may be calculated by multiplying the density of the medium by the square of the propagation speed of transverse waves. The signal processor 533 may calculate the shear modulus as the elasticity, and may generate an ultrasound elasticity image based on the calculated elasticity. The ultrasound elasticity image may include a color that is predetermined according to the elasticity of ROI, and may be implemented by a spectral image that is displayed in a three dimensional image or waves. According to an embodiment, an elasticity image may be generated by using an external pressure, or by using an internal pressure, e.g. a pressure that is generated by blood vessels adjacent to the cervix.

The scan converter 535 may convert the converted ultrasound image information, which is input from the signal processor 533 or stored on the storage unit 537, into a general video signal that is for the display unit 550, and may transmit a general video signal to the volume rendering unit 539.

The storage unit 537 may temporarily or non-temporarily store the ultrasound image information converted by the signal processor 533.

The volume rendering unit 539 may perform volume rendering based on the video signal transmitted from the scan converter 535, generate a final result image by correcting rendered image information, and transmit the generated result image to the display unit 550.

The input unit 540 may be provided to allow a user to input a command related to an operation of the ultrasound imaging apparatus 1. The user may input or set an ultrasound diagnosis start command, a diagnosis mode selection command, e.g. Brightness-mode (B-mode), Motion-mode (M-mode), Doppler-mode (D-mode), elasticity mode, and three dimensional mode, and a ROI setting information including the size and location of the ROI.

The B-mode may display a cross-sectional image of the inside of the object, and may display a part in which an echo is strong and a part in which an echo is weak with a brightness difference. B-mode image may be formed based on information acquired from several tens to several hundreds of scan lines.

The M-mode may display how biological information (e.g. luminance information) about a certain part (M line) in the cross-sectional image (B-mode image) of the object is changed as time passes, with an image, and in general, a B-mode image and a M-mode image may be simultaneously displayed on a single screen so that a user is allowed to make correct diagnosis by comparing and analyzing two data.

The D-mode may represent an image by using Doppler effect that is the change in frequency of a sound emitted from a moving object. The D-mode that uses the Doppler effect may be divided into Power Doppler Imaging mode (PDI-mode), color flow mode (S flow) and DPDI mode.

The PDI mode may display an intensity of Doppler signal or the number of structure (red blood cell in the blood) with an image, and because of being less sensitive about an incident angle the PDI mode may have no-aliasing effect and less image attenuation caused by the noise. In addition, since the PDI mode records reflected Doppler energy, the PDI mode may be very sensitive so as to detect a small blood vessel and a blood flow having a slow speed.

The color flow mode (S Flow) may provide a PDI indicating a power of Doppler signal in two dimensional distribution, and a velocity image indicating a velocity of the Doppler signal in two dimensional distribution. As well as the S Flow image may visualize a blood flow in real time, the S Flow image may display a comprehensive condition of the blood flow including from a high velocity of blood flow in the big blood vessel to a low velocity of blood flow in the small blood vessel.

The DPDI mode may represent a direction image indicating direction information of Doppler signal in two dimensional distribution. Therefore, in the DPDI mode, there may be an effect of detecting information about the blood flow more correct than the PDI mode. In addition, the M-mode image may be generated about the D-mode image.

The elasticity mode may represent a method of acquiring an ultrasound elasticity image of an object by using Elastography. The Elastography may be configured to analyze that a difference in the denaturalization of the tissue is reduced since as a tissue, e.g. a malignant tumor is harder, the elasticity of the structure is decreased. The ultrasound elasticity image may represent an image indicating the stiffness of the tissue in the quantity. Particularly, the elasticity mode may be widely used in the examination, e.g. an examination for the cervix, the breast cancer or the prostate cancer.

The three dimension mode may represent an image indicating a geometric solid or space including X, Y, and Z value representing a depth, an area and a height, and may represent a series of images indicating a three-dimensional sense or a three-dimensional effect as a three dimensions shape. For example, by using the three-dimensional effect of the three dimension mode, a user may display a shape of the fetus's face and may provide the fetus's face to the parent.

The input unit 540 may include a variety of tools configured to allow a user to input data and, an instruction and a command, e.g. a key board, a mouse, a trackball, a tablet or a touch screen module.

The display unit 550 may display a menu and a guidance that is needed for the ultrasound diagnosis, and an ultrasound image that is acquired in the ultrasound diagnosis procedure. The display unit 550 may display an ultrasound image of a target part in the inside of the object that is generated in the image processor 530. The ultrasound image displayed in the display unit 550 may be an ultrasound image in the B-mode, the elasticity mode, or the three dimension mode. The display unit 550 may display a variety of ultrasound images according to the above-mentioned modes. When displaying an ultrasound elasticity image, the display unit 550 may display a color that is predetermined according to the elasticity (i.e. shear modulus) of each point of a ROI. For example, the display unit 550 may indicate a point in which the elasticity is low, e.g. a tumor, as a red color, and a point in which the elasticity is high as a green color in the ultrasound elasticity image. The predetermined color is not limited to a red color and a green color, but the predetermined color may be set in various color according to the user' setting. In addition, the display unit 550 may display the elasticity of each point of the ROI that is digitized to a user.

The display unit 550 may be implemented by a variety of display method, e.g. Cathode Ray Tube (CRT), and Liquid Crystal Display (LCD).

According to an embodiment, as illustrated in FIG. 2, the probe (P) may include a transducer array (TA), a T/R switch 10, a transmission device 100, and a reception device 200. The transducer array (TA) may be provided in an end portion of the probe (P). The ultrasound transducer array (TA) may represent a plurality of ultrasound transducer elements 60 disposed in one-dimensional or two dimensional array. The ultrasound transducer array (TA) may generate ultrasound by being vibrated by applied pulse signal or A.C. The ultrasound generated in the ultrasound transducer array (TA) may be transmitted to a plurality of target parts in the inside of the object as a point. That is, the generated ultrasound may be transmitted to the plurality of target parts by multi-focusing.

The ultrasound generated in the ultrasound transducer array (TA) may be reflected by the target part in the inside of the object and then return to the ultrasound transducer array (TA). The ultrasound transducer array (TA) may receive an ultrasound echo signal that returns after being reflected by the target part. When the ultrasound echo signal is reached, the ultrasound transducer array (TA) may be vibrated with a certain frequency corresponding to a frequency of the ultrasound echo signal, and output A. C corresponding to the vibration frequency. Accordingly, the ultrasound transducer array (TA) may convert the received ultrasound echo signal into a certain electrical signal. Since each element 60 receives the ultrasound echo signal and output an electrical signal, the ultrasound transducer array (TA) may output an electrical signal in a plurality of channels.

The ultrasound transducer may be implemented by any one of a magnetostrictive ultrasonic transducer using the magnetostrictive effect of a magnetic material, a piezoelectric ultrasonic transducer using the piezoelectric effect of a piezoelectric material, or a capacitive micromachined ultrasonic transducer (cMUT) that transmits and receives ultrasonic waves using vibration of several hundreds or thousands of micromachined thin films. In addition, transducers configured to generate an ultrasound according to an electrical signal or configured to generate an electrical signal according to an ultrasound may be employed as an example of the ultrasound transducer.

For example, according to an embodiment, the ultrasound transducer element 60 may include a piezoelectric resonator or a thin film. When A.C is applied from the power source, the piezoelectric resonator or the thin film may be vibrated with a certain frequency according to the applied A.C and generate an ultrasound with a certain frequency according to the vibration frequency. Conversely, when an ultrasound echo signal with a certain frequency is received to the piezoelectric resonator or the thin film, the piezoelectric resonator or the thin film may be vibrated according to the ultrasound echo signal and output A.C with a frequency corresponding to the vibration frequency.

The transmission device 100 may apply a transmission pulse to the ultrasound transducer array (TA) and allow the ultrasound transducer array (TA) to transmit an ultrasound signal to a target part in the inside of the object. The transmission device may include a transmission beamformer and a pulser.

A transmission beamformer 110 may form a transmission signal pattern according to a control signal of the body (M) of the controller 500, and output the transmission signal pattern to a pulser 120. The transmission beamformer 110 may form a transmission signal pattern based on a time delay value about each of the ultrasound transducer elements 60 forming the ultrasound transducer array (TA) that is calculated by the controller 500, and transmit the formed transmission signal pattern to the pulser 120.

The reception device may perform a certain process about the ultrasound echo signal received by the ultrasound transducer array (TA) and perform a transmission beamforming. The reception device 200 may include a reception signal processor and a reception beamformer. An electrical signal converted in the ultrasound transducer array (TA) may be input to the reception signal processor. The reception signal processor may amplify an electrical signal that is converted from the ultrasound echo signal, adjust a gain or compensate attenuation according to the depth before performing a signal processing or a time delay processing. Particularly, the reception signal processor may include a low noise amplifier (LNA) configured to reduce a noise in an electrical signal input from the ultrasound transducer array (TA) and a variable gain amplifier (VGA) configured to control gain value according to an input signal. The VGA may employ Time Gain compensation (TGC) configured to compensate a gain according to a distance from a focal point, but is not limited thereto.

The reception beamformer may perform a beamforming on an electrical signal input from the reception signal processor. The reception beamformer may strengthen an intensity of the signal through a method of superposition of electrical signal input from the reception signal processor. A beamformed signal by the reception beamformer may be converted into a digital signal by passing through an analog/digital converter, and transmitted to the image processor 530 of the body (M). When the analog/digital converter is provided in the body (M), an analog signal in which a beamforming is performed through the reception beamformer may be transmitted to the body (M) and converted into a digital signal in the body (M). The reception beamformer may be a digital beamformer. The digital beamformer may include a storage unit configured to sample an analog signal and store the analog signal, a sampling period controller configured to control a sampling period, an amplifier configured to adjust the size of the sample, an anti-aliasing low pass filter configured to prevent aliasing before sampling, a band pass filter configured to select a desired frequency band, an interpolation filter configured to increase a sampling rate when performing a beamforming, and a high-pass filter configured to remove a DC component or a signal in the low frequency band.

Figure 4:
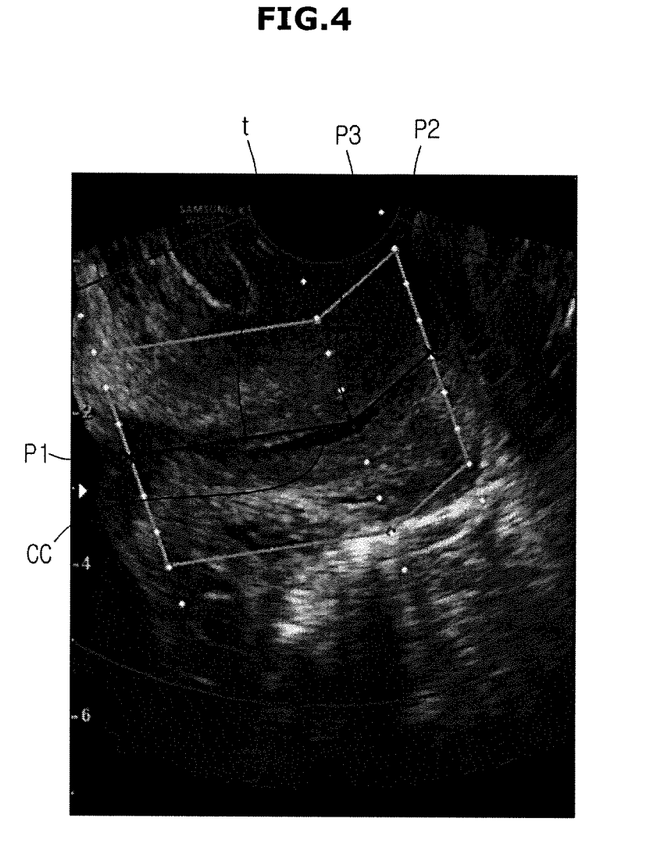
FIG. 4 is a view illustrating a point, which is a base to set a region of interest and included in a path corresponding to the cervix canal displayed on an ultrasound elasticity image in accordance with an embodiment of the present disclosure.
Figure 5:
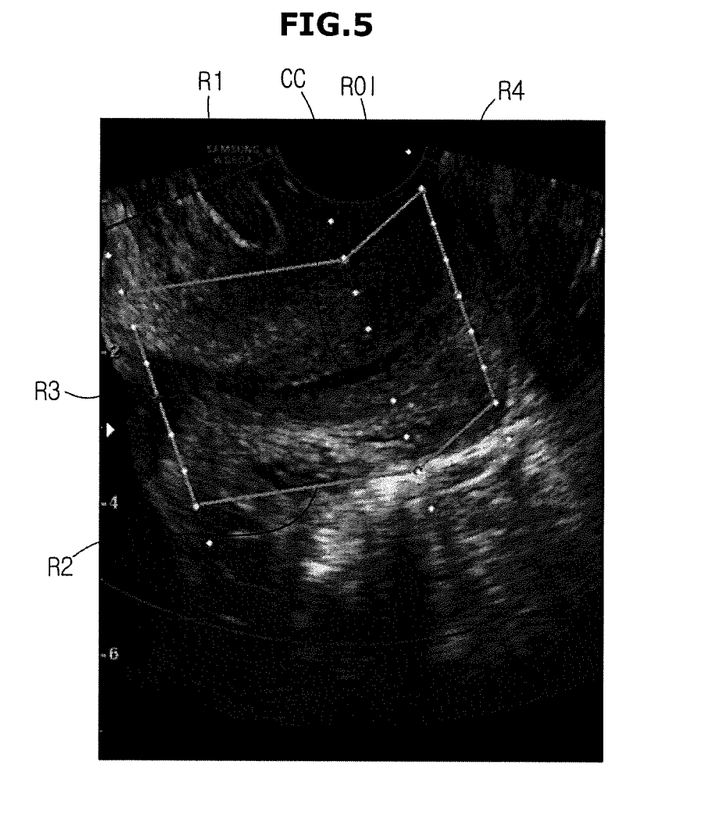
FIG. 5 is a view illustrating a region of interest having a shape corresponding to a shape of the cervix canal displayed on an ultrasound elasticity image in accordance with an embodiment of the present disclosure.

As mentioned above, according to an embodiment, the ultrasound imaging apparatus may set a ROI to a shape corresponding to a shape of an object of interest without simply setting the ROI to a circle or a square shape including the object of interest in an ultrasound elasticity image. For example, in an ultrasound elasticity image of the cervix, the ultrasound imaging apparatus may set a ROI having a shape corresponding to a shape of an object of interest that is the cervix, and may display the ROI in the ultrasound elasticity image displayed on the display unit. FIG. 4 is a view illustrating a point, which is the basis to set a region of interest and included in a path corresponding to the cervix canal displayed on an ultrasound elasticity image in accordance with an embodiment of the present disclosure and FIG. 5 is a view illustrating a region of interest having a shape corresponding to a shape of the cervix canal displayed on an ultrasound elasticity image in accordance with an embodiment of the present disclosure.

An ultrasound elasticity image of FIG. 4 is an elasticity image of the cervix and a ROI including the cervix may be set to acquire elasticity information of the cervix.

According to an embodiment, the ultrasound imaging apparatus may receive an input of a command that is the basis of setting a ROI via the input unit. In addition, when the display unit is provided with a touch panel, a command may be input by a touch via the display unit.

As illustrated in FIG. 4, the cervix canal displayed on the ultrasound elasticity image may have a curved shape. When a ROI is set in a conventional manner, the ROI may be set to a circle shape or a square shape, which does not correspond to a shape of an object of interest, without considering the shape of the object of interest, e.g. the cervix. When the ROI is set to have a shape that is different from the shape of the object of interest, it may be difficult to acquire more correct elasticity information of the cervix. According to an embodiment, a command may be received through the input unit to set a ROI corresponding to the shape of the cervix displayed in the ultrasound elasticity image. That is, as illustrated in FIG. 4, a command, which is to select a plurality of points passing a path corresponding to the shape of the cervix canal, may be received through the input unit.

Anatomically, a start and an end of the cervix correspond to an external orifice of the uterus and an internal orifice of the uterus, respectively. Therefore, in the ultrasound elasticity image, when a command to select a point (P1) corresponding to the internal orifice of the uterus and a point (P2) corresponding to the external orifice of the uterus is received, the controller may calculate a path of the cervix canal by using the selected point. For example, the controller may calculate a line connecting the external orifice of the cervix to the internal orifice of the cervix, as a path of the cervix canal. When the cervix is curved as mentioned above, a command, which is to select a curved point (P3) additionally, may be received to calculate a path corresponding to the shape of the cervix canal. That is, when a command to select the point (P2) corresponding to the external orifice of the uterus, the point (P1) corresponding to the internal orifice of the uterus, and the curved point (P3) is received, the controller may determine a path (t) corresponding to the cervix canal having the curved shape.

As mentioned above, the external orifice of the cervix, the internal orifice of the cervix, and the curved point are selected to determine a path corresponding to the cervix canal, but the selected points are not limited thereto.

The controller may help a user's selection by determining an appropriate point to generate a path corresponding to the cervix canal and displaying the point on the display unit. In this case, the controller may determine at least point including a point that is determined as a feature point of the shape of the cervix canal, e.g. the above-mentioned curved point, and display the point on the display unit. The user may select a point displayed on the display unit or another point. In addition, the controller may automatically generate a path corresponding to the cervix canal without inputting via the input unit, and set a ROI based on the path.

As mentioned above, when a plurality of points of the cervix canal is selected via the input unit, the controller may generate a path corresponding to the shape of the cervix canal by using the selected point, and set a ROI by using the generated path. The generated path may be displayed on an ultrasound elasticity image or may be not displayed according to the user' setting.

As illustrated in FIG. 5, the controller may generate a boundary having a shape corresponding to the path and being spaced apart with respect to the path corresponding to the cervix canal with a predetermined distance in directions that are opposite to each other, and may generate a ROI by connecting the generated boundary. The distance between the path and the boundary may be pre-determined based on the anatomical information of the cervix. Referring to an image displayed on FIG. 5, the ROI may be displayed to have a polygonal shape formed by an upper boundary (R1) having the same shape as the path, a lower boundary (R2) having the same shape as the path, a left boundary (R3) and a right boundary (R4) connecting the upper boundary to the lower boundary, on the display unit. The above mentioned method of setting ROI may be applied to a three dimensional ultrasound image. A user may adjust the shape and the size of the ROI that is displayed on the display unit through an input of command via the input unit or through an input of command by a touch via the display unit.

As illustrated in FIG. 5, when a ROI corresponding to the shape of the cervix is set, elasticity information of the cervix having more reliability may be calculated.

Figure 6:
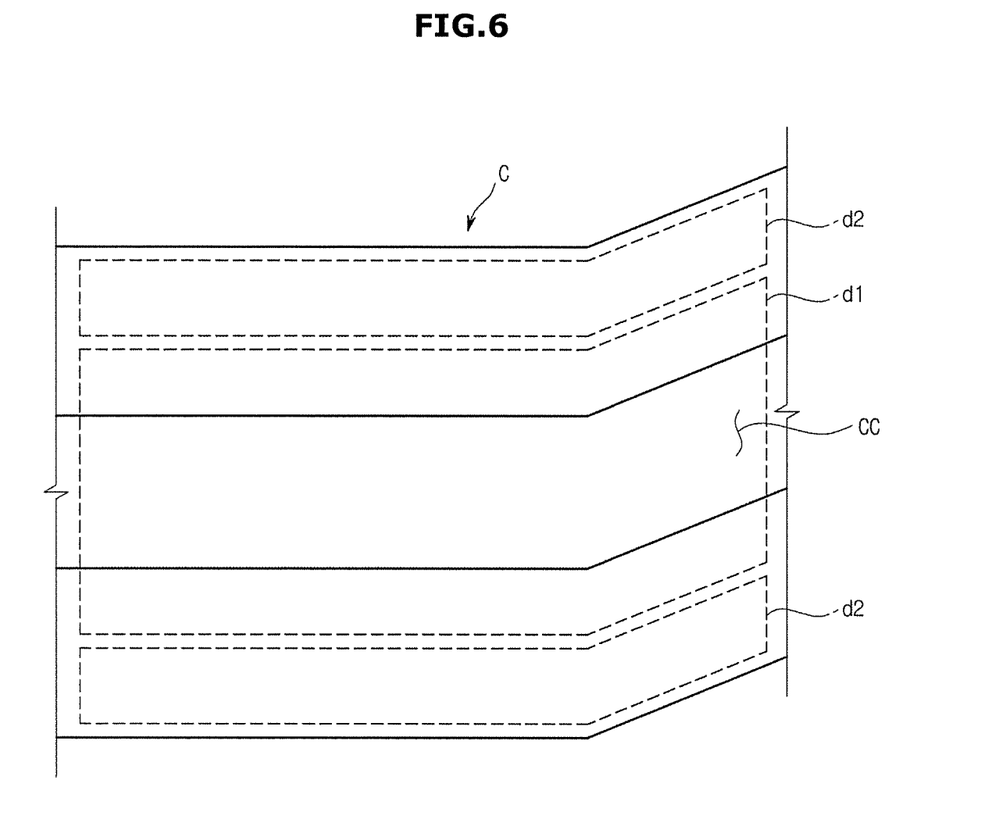
FIG. 6 is a view illustrating a region that is set to acquire elasticity information of the cervix in accordance with an embodiment of the present disclosure.

FIG. 6 is a view illustrating a region that is set to acquire elasticity information of the cervix in accordance with an embodiment of the present disclosure.

FIG. 6 schematically illustrates the shape of the cervix (c). In FIG. 6, the cervix canal is referred to as "cc", and the outside of the cervix canal may represent the tissue surrounding the cervix canal.

When the ROI is set, the controller may calculate an elasticity value of a first region (d1) including the cervix canal and a part of surrounding tissue of the cervix canal and an elasticity value of a second region (d2) of the outside of the first region, and then may calculate a ratio of the elasticity value of the first region and the elasticity value of the second region. The risk of the premature birth may be determined by using elasticity information of the cervix, and the elasticity information that is calculated according to the method illustrated in FIG. 6 may be used as a more correct index to determine the risk of the premature birth.

The controller may calculate an elasticity value of the external orifice of the uterus, an elasticity value of the internal orifice of the uterus, and a ratio of the elasticity value of the external orifice of the uterus and the elasticity value of the internal orifice of the uterus, and may calculate an elasticity value and a ratio of a certain region included in the ROI, or a ratio of elasticity value distribution region, as well as the above mentioned elasticity information. The information may be displayed on the display unit.

Figure 7:
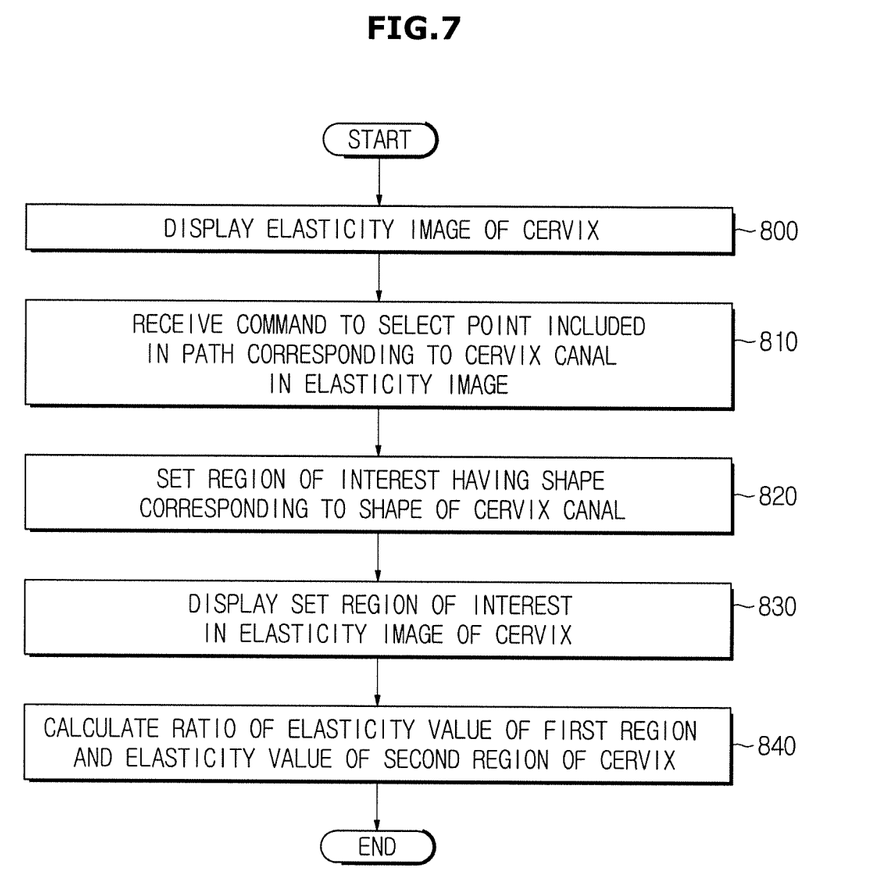
FIG. 7 is a flow chart illustrating a control method of an ultrasound imaging apparatus in accordance with an embodiment of the present disclosure.

FIG. 7 is a flow chart illustrating a control method of an ultrasound imaging apparatus in accordance with an embodiment of the present disclosure.

Referring to FIG. 7, in a state in which an ultrasound elasticity image of the cervix is displayed on the display unit (800), when a command to select a point included in a path corresponding to the cervix canal in the elasticity image is received (810), the controller may set a ROI having a shape corresponding to the shape of the cervix canal (820), and may display the ROI in the ultrasound elasticity image of the cervix (830).

As illustrated in FIG. 4, the cervix canal displayed on the ultrasound elasticity image may have a curved shape. When a ROI is set in a conventional manner, the ROI may be set to a circle shape or a square shape, which does not correspond to a shape of an object of interest, without considering the shape of the object of interest, e.g. the cervix. When the ROI is set to have a shape that is different from the shape of the object of interest, it may be difficult to acquire more correct elasticity information of the cervix. According to an embodiment, a command may be received through the input unit to set a ROI corresponding to the shape of the cervix displayed in the ultrasound elasticity image. That is, as illustrated in FIG. 4, a command, which is to select a plurality of points passing a path corresponding to the shape of the cervix canal, may be received through the input unit.

Anatomically, a start and an end of the cervix correspond to an external orifice of the uterus and an internal orifice of the uterus, respectively. Therefore, in the ultrasound elasticity image, when a command to select a point (P1) corresponding to the internal orifice of the uterus and a point (P2) corresponding to the external orifice of the uterus is received, the controller may calculate a path of the cervix canal by using the selected point. For example, the controller may calculate a line connecting the external orifice of the cervix to the internal orifice of the cervix, as a path of the cervix canal. When the cervix is curved as mentioned above, a command, which is to select a curved point (P3) additionally, may be received to calculate a path corresponding to the shape of the cervix canal. That is, when a command to select the point (P2) corresponding to the external orifice of the uterus, the point (P1) corresponding to the internal orifice of the uterus, and the curved point (P3), is received, the controller may determine a path (t) corresponding to the cervix canal having the curved shape.

As mentioned above, the external orifice of the cervix, the internal orifice of the cervix, and the curved point are selected to determine a path corresponding to the cervix canal, but the selected points are not limited thereto.

The controller may help a user's selection by determining an appropriate point to generate a path corresponding to the cervix canal and displaying the point on the display unit. In this case, the controller may determine at least point including a point that is determined as a feature point of the shape of the cervix canal, e.g. the above-mentioned curved point, and display the point on the display unit. The user may select a point displayed on the display unit or another point. In addition, the controller may automatically generate a path corresponding to the cervix canal without inputting via the input unit, and set a ROI based on the path.

As mentioned above, when a plurality of points of the cervix canal is selected via the input unit, the controller may generate a path corresponding to the shape of the cervix canal by using the selected point, and set a ROI by using the generated path. The generated path may be displayed on an ultrasound elasticity image or may be not displayed according to the user' setting.

As illustrated in FIG. 5, the controller may generate a boundary having a shape corresponding to the path and being spaced apart with respect to the path corresponding to the cervix canal with a predetermined distance in directions that are opposite to each other, and may generate a ROI by connecting the generated boundary. The distance between the path and the boundary may be pre-determined based on the anatomical information. Referring to an image displayed on FIG. 5, the ROI may be displayed to have a polygonal shape formed by an upper boundary (R1) having the same shape as the path, a lower boundary (R2) having the same shape as the path, a left boundary (R3) and a right boundary (R4) connecting the upper boundary to the lower boundary, on the display unit. The above mentioned method of setting ROI may be applied to a three dimensional ultrasound image. A user may adjust the shape and the size of the ROI that is displayed on the display unit through an input of command via the input unit or through an input of command by a touch via the display unit.

When the ROI is set, the controller may calculate a ratio of the elasticity value of the first region of the cervix and the elasticity value of the second region of the cervix (840).

FIG. 6 schematically illustrates the shape of the cervix. In FIG. 6, the cervix canal is referred to as "cc", and the outside of the cervix canal may represent the tissue surrounding the cervix canal.

When the ROI is set, the controller may calculate the elasticity value of the first region (d1) including the cervix canal and a part of surrounding tissue of the cervix canal and the elasticity value of the second region (d2) of the outside of the first region, and then may calculate the ratio of the elasticity value of the first region and the elasticity value of the second region. The risk of the premature birth may be determined by using elasticity information of the cervix, and the elasticity information that is calculated according to the method illustrated in FIG. 6 may be used as a more correct index to determine the risk of the premature birth.

The controller may calculate the elasticity value of the external orifice of the uterus, the elasticity value of the internal orifice of the uterus, and the ratio of the elasticity value of the external orifice of the uterus, the elasticity value of the internal orifice of the uterus, and may calculate the elasticity value or the ratio of a certain region included in the ROI, as well as the above mentioned elasticity information. The information may be displayed on the display unit.

Although a few embodiments of the present disclosure have been shown and described, it would be appreciated by those skilled in the art that changes may be made in these embodiments without departing from the principles and spirit of the disclosure, the scope of which is defined in the claims and their equivalents.

The invention claimed is:

1. An ultrasound imaging apparatus comprising:
 a display unit configured to display an ultrasound elasticity image of a cervix;
 a controller configured to control the display unit to display feature points corresponding to a shape of a cervix canal in the ultrasound elasticity image of the cervix;
 an input unit configured to receive a command to select a point (P2) corresponding to an external orifice of a uterus, a point (P1) corresponding to an internal orifice of the uterus and a point (P3) on a curved portion of the cervix among the feature points; and
 wherein the controller is configured to:
  generate a path of the cervix canal as a line by connecting the point (P2) corresponding to the external orifice of the uterus, the point (P1) corresponding to the internal orifice of the uterus, and the point (P3) on the curved portion of the cervix,
  generate a plurality of boundaries having a shape corresponding to the path and being spaced apart with respect to the path of the cervix canal with a predetermined distance in directions that are opposite to each other,
  set a region of interest having a shape corresponding to a shape of the cervix canal by connecting the plurality of boundaries, and
  control the display unit to display the region of interest.

2. The ultrasound imaging apparatus of claim 1, wherein the controller calculates elasticity information including a ratio of an elasticity value of a first region including the cervix canal in the region of interest and an elasticity value of a second region that is outside of the first region.

3. The ultrasound imaging apparatus of claim 2, wherein the controller calculates an elasticity value of the first region including the cervix canal in the region of interest.

4. The ultrasound imaging apparatus of claim 1, wherein the controller calculates an elasticity value of the external orifice of the uterus, an elasticity value of the internal orifice of the uterus, and a ratio of the elasticity value of the external orifice of the uterus and the elasticity value of the internal orifice of the uterus.

5. A control method of an ultrasound imaging apparatus comprising:
 displaying an ultrasound elasticity image of a cervix;
 displaying feature points corresponding to a shape of a cervix canal in the ultrasound elasticity image of the cervix;
 receiving a command to select a point (P2) corresponding to an external orifice of a uterus, a point (P1) corresponding to an internal orifice of the uterus and a point (P3) on a curved portion of the cervix among the feature points;
 generating a path of the cervix canal as a line by connecting the point (P2) corresponding to the external orifice of the uterus, the point (P1) corresponding to the internal orifice of the uterus and the point (P3) on the curved portion of the cervix;
 generating a plurality of boundaries having a shape corresponding to the path and being spaced apart with respect to the path of the cervix canal with a predetermined distance in directions that are opposite to each other;
 setting a region of interest having a shape corresponding to a shape of the cervix canal by connecting the plurality of boundaries; and
 displaying the set region of interest on a display unit.

6. The control method of claim 5, further comprising:
 calculating elasticity information including a ratio of an elasticity value of a first region including the cervix canal in the region of interest and an elasticity value of a second region that is outside of the first region.

7. The control method of claim 5, further comprising:
 calculating an elasticity value of a first region including the cervix canal in the region of interest.

8. The control method of claim 5, further comprising:
 calculating an elasticity value of the external orifice of the uterus, an elasticity value of the internal orifice of the uterus, and a ratio of the elasticity value of the external orifice of the uterus and the elasticity value of the internal orifice of the uterus.

* * * * *